(12) United States Patent
Inagaki

(10) Patent No.: US 7,481,094 B2
(45) Date of Patent: Jan. 27, 2009

(54) GAS SENSOR CONTROL UNIT

(75) Inventor: Hiroshi Inagaki, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 321 days.

(21) Appl. No.: 11/393,840

(22) Filed: Mar. 31, 2006

(65) Prior Publication Data

US 2006/0219555 A1    Oct. 5, 2006

(30) Foreign Application Priority Data

Mar. 31, 2005    (JP) .............................. 2005-104519

(51) Int. Cl.
*G01N 7/00* (2006.01)
*G06F 7/00* (2006.01)

(52) U.S. Cl. ..................... 73/23.32; 701/109

(58) Field of Classification Search ................ 73/23.32; 701/190
See application file for complete search history.

(56) References Cited

U.S. PATENT DOCUMENTS

| | | | |
|---|---|---|---|
| 4,064,498 A | 12/1977 | Burr et al. | |
| 4,290,107 A * | 9/1981 | Suda et al. | ................... 701/109 |
| 5,298,865 A | 3/1994 | Denz et al. | |
| 5,454,259 A | 10/1995 | Ishii et al. | |
| 5,541,601 A | 7/1996 | Goto et al. | |
| 5,908,600 A | 6/1999 | Simi et al. | |
| 6,120,677 A | 9/2000 | Yamada et al. | |
| 6,245,205 B1 | 6/2001 | Schnaibel et al. | |
| 2002/0162743 A1 | 11/2002 | Inagaki | |
| 2004/0222094 A1 | 11/2004 | Ieda et al. | |
| 2006/0049843 A1 * | 3/2006 | Jenkins et al. | ............... 324/765 |
| 2006/0132881 A1 | 6/2006 | Kim | |

FOREIGN PATENT DOCUMENTS

| | | |
|---|---|---|
| DE | 102 54 852 A1 | 6/2004 |
| EP | 0 688 945 A2 | 12/1995 |
| EP | 1 460 418 A1 | 9/2004 |
| JP | 2-47561 | 3/1990 |
| JP | 5-107299 | 4/1993 |
| JP | 6-324811 | 11/1994 |
| JP | 7-43336 | 2/1995 |
| JP | 7-83867 | 3/1995 |
| JP | 10-48180 | 2/1998 |
| JP | 11-304758 | 11/1999 |
| JP | 2000-65779 | 3/2000 |
| JP | 2000-81414 | 3/2000 |
| JP | 2000-92083 | 3/2000 |
| JP | 2002-71640 | 3/2002 |
| JP | 2004-285949 | 10/2004 |
| JP | 2004-301832 | 10/2004 |
| WO | WO 2004/048956 A1 | 6/2004 |

* cited by examiner

*Primary Examiner*—Hezron Williams
*Assistant Examiner*—John Fitzgerald
(74) *Attorney, Agent, or Firm*—Sughrue Mion, PLLC

(57) ABSTRACT

A gas sensor control unit (1) including a single signal-switching and outputting circuit (33) adapted for switching and outputting plural signals transmitted from plural gas sensors (8,9).

6 Claims, 5 Drawing Sheets

US 7,481,094 B2

GAS SENSOR CONTROL UNIT

BACKGROUND OF THE INVENTION

1. The Field of the Invention:

The present invention generally relates to a gas sensor control unit for electrically connecting plural gas sensors with an external apparatus such as an ECU (engine control unit). The plural gas sensors detect and transmit via the gas sensor control unit gas concentration signals of specific gas components exhausted from an internal combustion engine to the external apparatus for controlling fuel-combustion in the engine. In particular, the present invention relates to a gas sensor control unit capable of transmitting gas-detection signals detected by plural gas sensors and internal resistance signals thereof to the external apparatus for controlling an air/fuel ratio of an internal combustion engine, the plural gas sensors each comprising a gas-sensing solid electrolyte cell element.

2. Description of the Related Art:

A conventionally known gas sensor control unit adapted for connection to a gas sensor comprises a gas-sensing solid electrolyte cell, which unit detects a gas detection signal corresponding to a specific gas concentration (e.g., oxygen concentration) of an exhaust gas exhausted from an internal combustion engine and also detects an internal resistance signal corresponding to an internal resistance of the gas sensor element. The gas sensor control unit then outputs these signals to an engine control unit (ECU), as disclosed in Patent Documents 1 and 2.

The external apparatus performs various control functions including air/fuel ratio feedback control of the internal combustion engine and target temperature control of the gas sensor element, based on the gas detection signal and the internal resistance signal transmitted from the gas sensor control unit connected with the gas sensor.

[Patent Document 1] Japanese Patent Application Laid-Open (kokai) No. H10-0814140 (FIGS. 1 and 10)

[Patent Document 2] Japanese Patent Application Laid-Open (kokai) No. H10-048180 (FIG. 2)

3. Problems to be Solved by the Invention:

Conventionally, one known gas sensor control unit is provided for each gas sensor. In other words, a conventional gas sensor control unit is only capable of controlling or processing signals from a single gas sensor. Thus, when plural gas sensors are mounted in exhaust pipes of both cylinder banks as in a V-type engine compartment so as to accurately control an air/fuel ratio of the internal combustion engine, it is necessary to install plural gas sensor control units, depending on the number of gas sensors to be provided in the engine compartment.

Therefore, the use of plural gas sensor control units connecting plural gas sensors with an external apparatus causes an installation space problem in accommodating plural gas sensor control units in a space-limited engine compartment and an increase in cost. In addition, when plural gas sensor control units are installed in the engine compartment, an increased number of signal paths in a wiring harness between the plural gas sensor control units and the external apparatus becomes disadvantageously complicated. This is because every gas detection signal and every internal resistance signal of the plural gas sensors detected by the plural gas sensor control units is outputted to the external apparatus.

SUMMARY OF THE INVENTION

The present invention has been achieved to solve the above problems relating to the complicated signal paths of gas sensor control units adapted for connecting plural gas sensors to the external apparatus.

Therefore, an object of the present invention is to provide a gas sensor control unit capable of processing plural signal outputs from a plurality of gas sensors and simplifying signal paths between plural gas sensors and an external apparatus such as an ECU (engine control unit) to which the plural signals are transmitted via the gas sensor control unit.

The above object of the present invention has been achieved by providing (with reference to the attached drawings for the purpose of facilitating comprehension of the invention but which should not be construed as limiting the invention) a gas sensor control unit (1) adapted for connection to plural gas sensors including at least first and second gas sensors (8, 9), comprising:

first and second signal-detection circuits (51, 53) for detecting first and second gas-detection signals (VIp1, VIp2) and first and second internal resistance signals (Rpvs1, Rpvs2) of the first and second gas sensors (8, 9), respectively;

a signal-switching and outputting circuit (33) for receiving signals (Vs+1, Ip+1, COM1, Vs+2, Ip+2, COM2) including at least said first and second internal resistance signals (Rpvs1, Rpvs2), said signal-switching and outputting circuit switching the signals including at least said first and second internal resistance signals (Rpvs1, Rpvs2), and outputting at least one of the switched signals (RpVs1, RpVs2) to an external apparatus; and a switched-signal controlling circuit (35) for controlling said signal-switching and outputting circuit (33) and specifying the signals to be switched and outputted from the signal-switching and outputting circuit (33) to the external apparatus.

An important feature of the gas sensor control unit (1), according to the invention, is that a signal-switching and outputting circuit (33) that switches at least internal resistance signals (Rpvs1, Rpvs2) of plural gas sensors (8, 9) and outputs one of the switched signals to the external apparatus, is incorporated in the gas sensor control unit (1). In other words, the gas control unit (1) selectively or alternatively outputs the switched signals of the plural gas sensors to the external apparatus, the switched signals including the plural internal resistance signals (Rpvs1, Rpvs2). Preferably, the signal-switching and outputting circuit (33) switches two or more signals sent from the plural gas sensors and outputs the switched signals one by one in sequential order, through an output-switching terminal 41 to the external apparatus, based on an instruction sent from the switched-signal controlling circuit (35). An order for outputting one of the switched signals from the signal-switching and outputting circuit (33) may be originally given in a serial communication from the external apparatus to the switched-signal controlling circuit (35) which then sends to the signal-switching and outputting circuit (33) the instruction to output the switched signal.

The gas sensor control unit (1) incorporates a signal-switching and outputting circuit (33) that is capable of switching two or more signals including plural internal resistance signals (Rpvs1, Rpvs2) of plural gas sensor elements (8, 9) and outputting them to the external apparatus one by one in sequential order. Consequently, the signal paths for outputting at least the internal resistance signals (Rpvs1, Rpvs2) of the plural gas sensors (8, 9) to the external apparatus can advantageously be reduced in number and size, as compared to a conventional gas sensor control unit that does not have a signal-switching means for switching internal resistance signals (Rpvs1, Rpvs2) and transmitting or outputting at least one of them to the external apparatus. The signal paths include a wiring harness and converters for converting analog signals to digital signals. A common signal path for transmitting plural switched-digital signals including internal resistance signals (Rpvs1, Rpvs2) of plural different gas sensors can be utilized between the external apparatus and the gas sensor control unit (1), according to the invention. This common signal path includes a switched signal output terminal 41 provided in the gas sensor control unit (1).

As long as the signal-switching and outputting circuit (33) switches internal resistance signals of plural gas sensors (i.e., gas sensing elements each comprising a gas sensing solid electrolyte cell) (8, 9) inputted thereto from the plural signal-detection circuits (51, 53) and outputs them interchangeably to an external apparatus, it may also switch other signals including signals from the gas sensors and output them interchangeably or alternatively to the external apparatus.

In the meantime, when an internal combustion engine is equipped with the gas sensor control unit (1), an air-fuel ratio feedback control is performed in an external apparatus (e.g., ECU: engine control unit), based on the gas detection signals. However, if the gas detection signals detected by plural signal detection means (namely, plural signal detection circuits 51, 53) are switched and output interchangeably or alternatively by the signal-switching and outputting circuit (33) to the external apparatus in sequential order, the external apparatus can only sample each gas detection signal, vacating a certain time interval for sampling a next switched gas detection signal. Therefore, accurate air-fuel ratio feedback control capable of meeting recent toughened exhaust gas emission control regulations requiring improved fuel consumption efficiency may not be facilitated or fully attained.

Thus, in another aspect of the invention, the gas sensor control unit (1) according to the invention, preferably, further comprises a gas detection signal output means (43) for independently outputting plural gas detection signals (VIp1, VIp2) detected by the plural signal detection means (first and second signal detection circuits 51, 53) to the external apparatus without passing through the signal-switching and outputting circuit (33).

Thus, by including gas detection signal output means (43) that independently outputs plural gas-detection signals not via the signal-switching and outputting circuit (33), in addition to the signal-switching and outputting circuit (33) that switches at least internal resistance signals of plural gas sensors and outputs the switched internal resistance signals in sequential order, the gas sensor control unit (1) according to the invention may advantageously transmit plural gas-detection signals (VIp1, VIp2) either at comparatively long or short intervals so as to enable the external apparatus to advantageously recognize the gas detection signals (VIp1, VIp2) at any specific timing.

The gas sensor control unit (1) according to the present invention may independently output plural gas detection signals detected by way of the gas detection signal means, while selectively outputting one of internal resistance signals of the plural gas sensors or interchangeably outputting the plural signals including the internal resistance signals, which internal resistance signals have been switched by the signal-switching and outputting circuit (33). As a result, a simple configuration and reasonable cost of the gas sensor control unit are advantageously realized along with facilitating accurate air-fuel ratio control. In addition, the gas sensor control unit (1) according to the invention advantageously simplifies a wiring harness for signal paths between the gas sensor control unit (1) and an external engine control unit, compared to a conventional gas sensor control unit.

Next, in the gas sensor control unit (1) according to the invention, each of plural signal detection circuit (51, 53) includes a resistance signal retention means (resistance signal retention circuit 55 as referred to in FIG. 3) for holding a detected internal resistance signal (Rpvs1, Rpvs2) of its associated gas sensor element 8, 9, and outputting the internal resistance signals held by the resistance signal retention means to the signal-switching and outputting circuit (33) in sequential order.

The resistance signal retention means can hold the gas sensor element internal resistance signal. Thus, an output timing of the internal resistance signal of the gas sensor to be sent to the external apparatus can be set at any specific timing when an internal resistance value of the gas sensing element (8 or 9) in a specific period of time is to be output to the external apparatus, the resistance value varying over time.

Thereby, greater flexibility of the output timing of each internal resistance signal of the gas sensor elements is attained. Furthermore, the internal resistance signals of the gas sensor elements are output at any specific timing to the external apparatus such as an ECU, even when the two or more internal resistance signals of the plural gas sensors are switched and output one by one from the signal-switching and outputting circuit (33).

Next, the gas sensor control unit (1), according to the invention, may further comprise a signal assignment instruction receiving means for receiving a signal assignment instruction from the external apparatus, the signal assignment instruction specifying a switched output signal. Specifically, a switched-signal controlling circuit (35) for controlling the signal-switching and outputting circuit (33) receives a signal assignment instruction from an external apparatus, specifying which of the switched signals that is to be output as a switched output signal from the signal-switching and outputting circuit (33), based on the assignment instruction or order given to the switched-signal controlling circuit (35) from the external apparatus.

The gas sensor control unit according the invention preferably comprises a signal assignment instruction receiving means (switched-signal controlling circuit 35), which specifies the signal that the external apparatus requires as the switched output signal. Thus, the contents of the switched output signals communicated between the gas sensor control unit and the external apparatus can be synchronized.

In this case, the signal assignment instruction receiving means (switched-signal controlling circuit 35) may receive the signal assignment instruction by way of a serial communication from the external apparatus through serial communication terminals 45.

Since a large variety of signals can be communicated by way of the serial communication between the gas sensor control unit and the external apparatus, signals relating to the signal assignment instruction or order may be included in the large variety of signals. Therefore, the gas sensor control unit (1) does not require a separate signal path or independent signal line to be exclusively used for receiving and/or outputting the signal assignment instructions. Therefore, a simple and cost competitive gas sensor control unit can be produced.

Next, the gas sensor control unit (1) according to the invention may further comprise: an anomaly detection means (an anomaly-detection circuit 37) for detecting a voltage anomaly appearing at any of plural connecting points connecting the signal detection means (the first and second signal detection circuits 51, 53) with the plural gas sensors (8, 9). Specifically the anomaly detection means may include a voltage anomaly notification means for outputting a voltage anomaly notification signal notifying the external apparatus of the occurrence of the voltage anomaly (when a voltage anomaly at any of the plural connecting points is detected by the anomaly detection means).

In this gas sensor control unit (1), the signal-switching and outputting means (: the signal-switching and outputting circuits 33) receives plural voltage signals each corresponding to a voltage detected at a connecting point connecting a first or second gas sensor (8, 9) with the signal detection means (first or second signal detection circuit 51 or 53). The signal-switching and outputting means also receives a signal assignment instruction from the switched-signal controlling circuit (35), the signal assignment instruction originally being given from an external apparatus through serial communication terminals (45). Plural point voltage signals (Vs+1, COM1, Ip+1, Vs+2, COM2, Ip+2) each corresponding to a voltage value of respective plural connecting points are input into the signal-switching and outputting circuit (33). The signal assignment instruction is received by the signal-switching and outputting circuit 33, which instruction specifies at least one of the voltage point signals to be output as a switched output signal therefrom, based on the signal order of the external apparatus to which the anomaly notification signal is notified thorough the serial communication terminals 45.

In the meantime, in the gas sensor control unit capable of notifying the external apparatus of the occurrence of a voltage anomaly at a connecting point between the signal detection means and the gas sensors, every connecting point voltage signal may regularly be outputted. However, the gas sensor control unit does not necessarily output the connecting point voltage signal on a regular frequent basis, because the frequency of occurrence of the voltage anomaly occurring at the connecting point is very low. In other words, the connecting point voltage signal is necessarily output only when a voltage anomaly occurs.

The external apparatus is notified of the occurrence of the voltage anomaly by the anomaly detection means (anomaly-detection circuit 37) which includes the voltage anomaly notification means.

Since the gas sensor control unit (1) according to the invention can switch and output plural connecting point voltage signals as the switched output signal, and can reduce the number of means and signal paths for outputting plural connecting point voltage signals to the external apparatus, a simple configuration and reasonable cost of the gas sensor control unit is attained.

Even if the plural connecting point voltage signals are necessarily output at the time that a voltage anomaly occurs at the connecting points, the gas sensor control unit can control two or more plural gas sensors with simplified signal paths connecting the sensor control unit and the external apparatus, as compared to a conventional control unit.

DESCRIPTION OF REFERENCE NUMERALS

Figure 1:
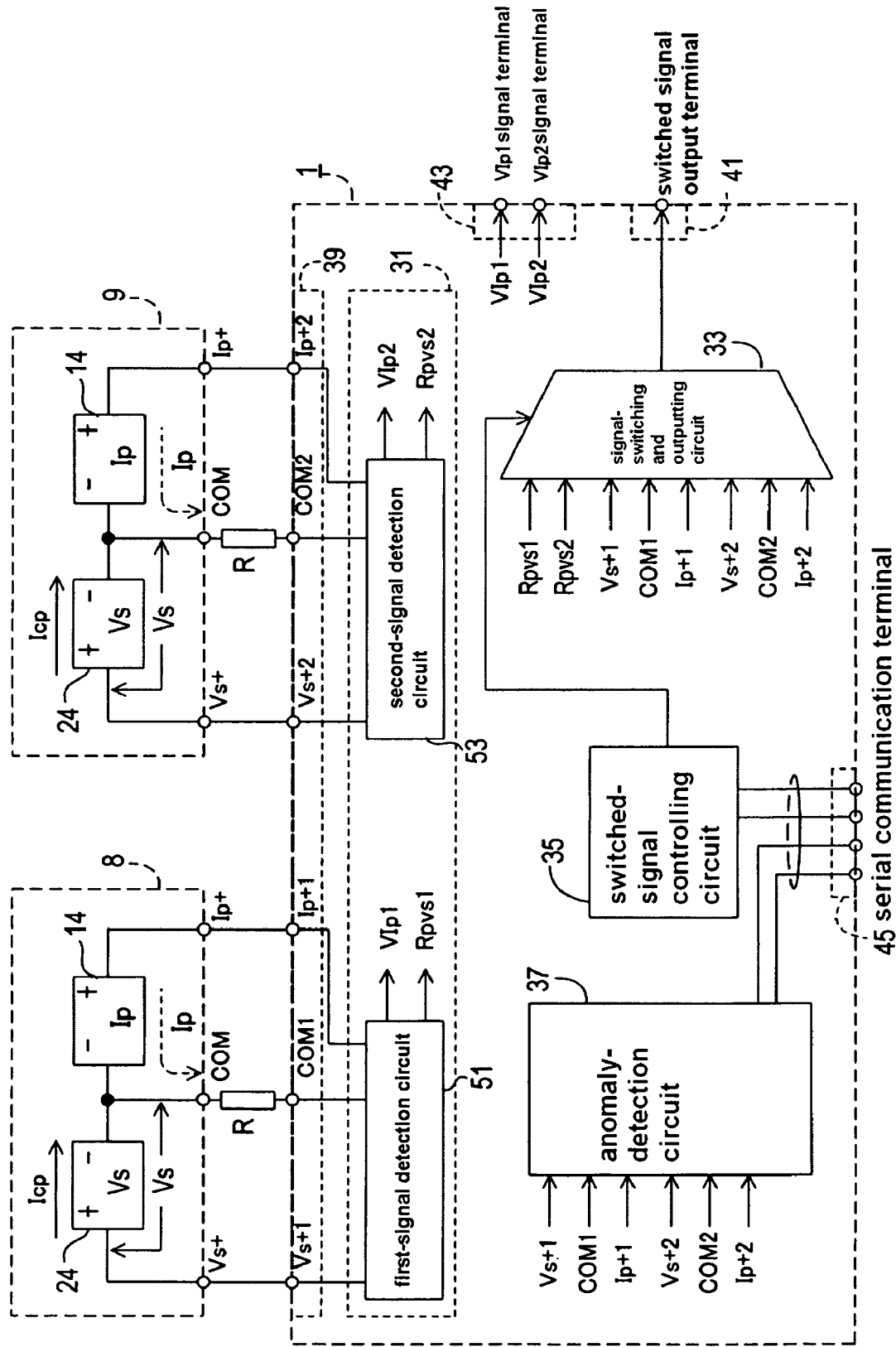
FIG. 1 is a schematic diagram showing a gas sensor control unit according to the invention.

Reference numerals used to identify various structural features shown in the drawings include the following.
1: gas sensor control unit
8, 9: first and second gas sensors (first and second gas sensor elements)
31: signal detection portion
33: signal-switching and outputting circuit
35: switched-signal controlling circuit
37: anomaly-detection circuit
39: sensor connection terminal portion
41: switched-signal output terminal
43: gas detection signal output terminal
45: serial communication terminal
51: first signal detection circuit
53: second signal detection circuit
55: signal retention circuit

DETAILED DESCRIPTION OF THE INVENTION

Embodiments of the present invention will next be described with reference to the drawings. However, the present invention should not be construed as being limited thereto.

A schematic circuit diagram of a gas sensor control unit 1 according to the present invention is shown in FIG. 1.

The gas sensor control unit 1 is connected to first and second gas sensor 8, 9 so as to detect gas-detection signals and internal resistance signals of the gas sensors 8, 9 that are respectively mounted in exhaust pipes of V-type engine banks, and outputs the gas detection signals and the internal resistance signals to an engine control unit.

Notably, the gas sensors 8, 9 can detect an oxygen concentration of an exhaust gas over a wide range, and the engine control unit performs an air-fuel ratio control, as one of its various controls, of each cylinder of the V-type engine, based on the oxygen concentration of the exhaust gas.

The gas sensor control unit 1 comprises a signal detection portion 31 comprising first and second circuits 51, 53, a signal-switching and outputting circuit 33, a switched-signal controlling circuit 35 and an anomaly-detection circuit 37. The gas sensor control unit 1 further comprises a sensor connection terminal portion 39, a switched-signal output terminal 41, gas detection signal terminals 43 and serial communication terminals 45.

The sensor connection terminal portion 39 comprises three terminals (Vs+1 terminal, COM 1 terminal, Ip+1 terminal) connected to a first gas sensor 8, and the other three terminals (Vs+2 terminal, COM2 terminal, Ip+2 terminal) connected to a second gas sensor 9.

The signal detection portion 31 comprises a first-signal detection circuit 51 connected to the first gas sensor 8 through the sensor connection terminal portion 39 and a second-signal detection circuit 53 connected to the second gas sensor 9 through the sensor connection terminal portion 39.

Figure 2:
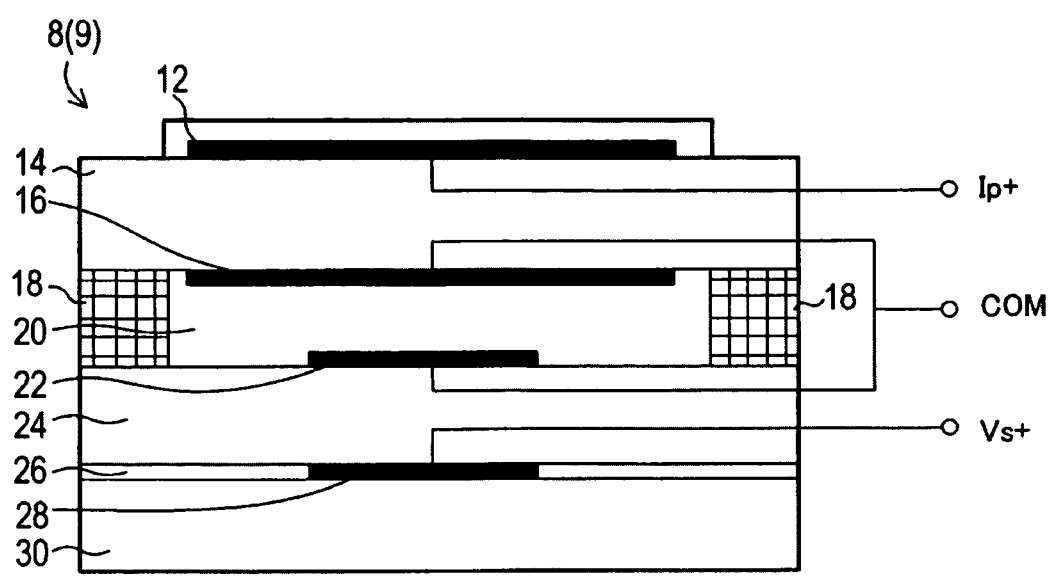
FIG. 2 is a schematic diagram showing a gas sensor.

Hereinafter, a gas sensor is described briefly with reference to a schematic view of the gas sensors 8 (9) in FIG. 2. The configuration and function of the first gas sensor 8 is substantially the same as the second gas sensor 9.

The gas sensors 8, 9 each comprises a superposed pump cell 14, a porous diffusion layer 18, an electromotive force cell 24 and a reinforcement plate 30.

The pump cell 14 comprises an oxygen ion-conductive solid electrolyte layer made of partially stabilized zirconia ($ZrO_2$), and porous platinum electrodes 12, 16 formed on top and bottom surfaces thereof, respectively. Similarly, the electromotive force cell 24 comprises an oxygen ion-conductive solid electrolyte layer made of partially stabilized zirconia ($ZrO_2$) and porous platinum electrodes 22, 28 formed on top and bottom surfaces thereof, respectively.

The porous electrode 16 exposed to a measuring chamber 20 of the pump cell 14 and the porous electrode 22 exposed to the measuring chamber 20 of the electromotive force cell 24 are electrically connected to each other as well as to each output terminal COM of the gas sensors 8, 9. In addition, each output terminal COM is connected to the COM 1 terminal or COM2 terminal of the sensor connection terminal portion 39 through a resistor R (referring to FIG. 1). Moreover, the porous electrode 12 of the pump cell 14 is connected to each output terminal Ip+ of the gas sensors 8, 9 and the porous electrode 28 of the electromotive force cell 24 is connected to each output terminal Vs+ of the gas sensors 8, 9. In addition, each output terminal Ip+ is connected to the Ip+1 terminal or Ip+2 terminal of the sensor connection terminal portion 39, and each output terminal Vs+ terminal is connected to the Vs+1 terminal or Vs+2 terminal of the sensor connection terminal portion 39 (referring to FIG. 1).

Moreover, the reinforcement plate 30 is laminated on the porous electrode 28 of the electromotive force cell 24 to form a closed oxygen reference chamber 26.

The measuring chamber 20 surrounded by a gas-diffusion limiting porous layer 18 is formed between the pump cell 14 and the electromotive force cell 24. That is, the measuring chamber 20 communicates with an external exhaust gas by way of the porous layer 18 that limits or rather controls the gas diffusing into the measuring chamber 20. The gas-diffusion limiting porous layer 18 is formed by partially filling a porous material at the inlet of the chamber 20.

Normally, the gas sensors 8, 9 are equipped with a heater that heats and activates the pump cell 14 and the electromotive force cell 24.

Figure 3:
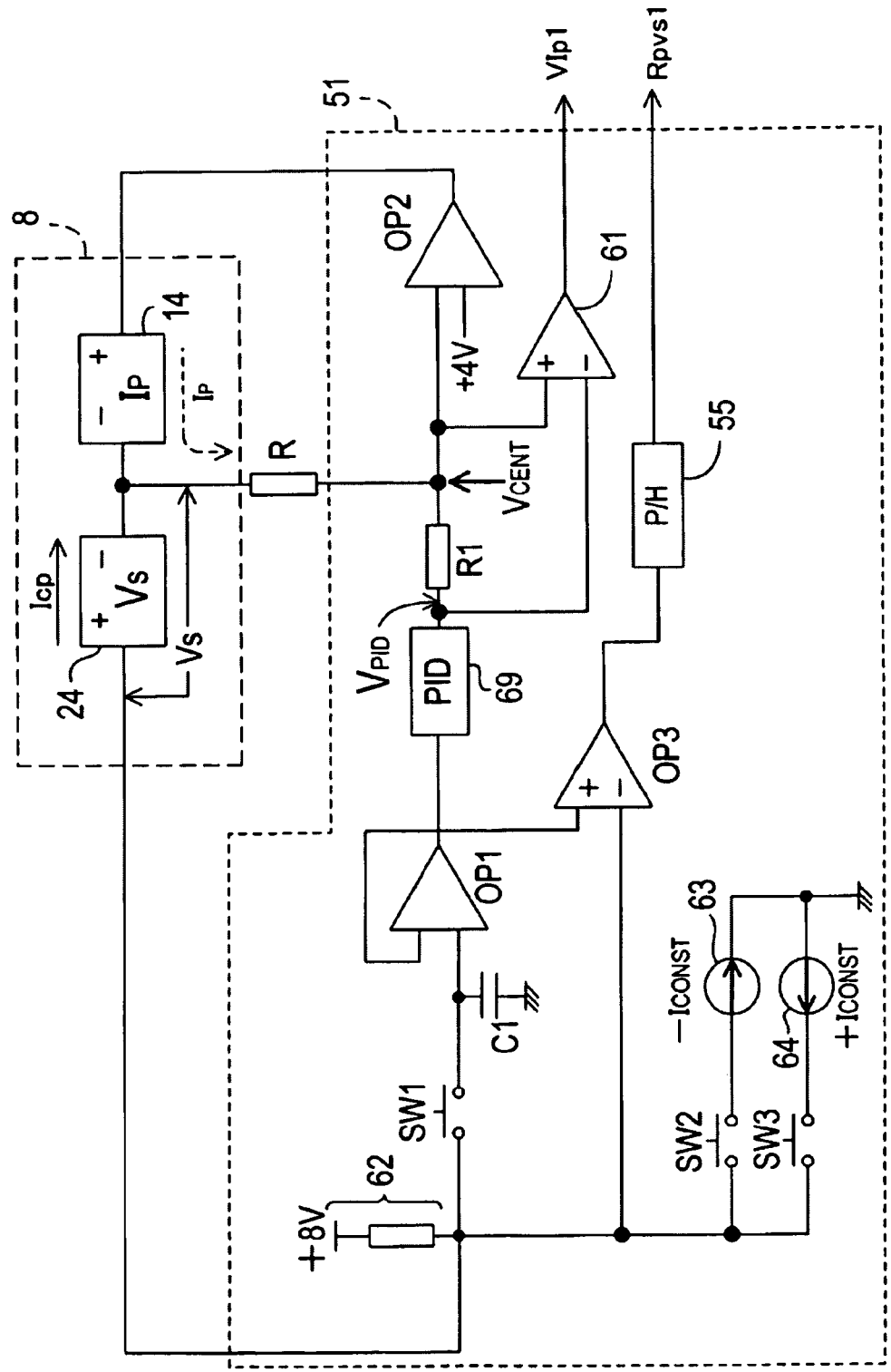
FIG. 3 is a circuit diagram showing the first-signal detection circuit where a gas sensor is connected.

Next, the first-signal detection circuit 51 in the signal detection portion 31 will be explained. A circuit diagram of a first-signal detection circuit 51 to which the first gas sensor 8 is connected is shown in FIG. 3. Notably, the second-signal detection circuit 53 has the same configuration as the first-signal detection circuit 51.

First, an operation of measuring the oxygen concentration in the first-signal detection circuit 51 will be explained by reference to FIG. 3.

In the first-signal detection circuit 51, a small constant current (Icp) generated by a constant current supply circuit 62 flows through the electromotive force cell 24, and the oxygen in the measuring chamber 20 is either pumped into or out by controlling pump current (Ip) flowing through the pump cell 14 so that the voltage (Vs) developed across the electrodes of the electromotive force cell 24 becomes 450 mV. Since the value and direction of the pump current (Ip) flowing in the pump cell 14 can vary, depending on the oxygen concentration of the exhaust gas, it is possible to compute the oxygen concentration of the exhaust gas based on the pump current (Ip). The oxygen reference chamber 26 functions as an internal oxygen reference source by passing a small electric current (Icp) through the electromotive force cell 24 in such a direction that oxygen in the measuring chamber 20 is pumped out to the porous electrode 28 side.

Further, the first-signal detection circuit 51 includes an operational amplifier OP1, an operational amplifier OP2, switches (SW1-SW3) and a PID control circuit 69 in addition to the constant current supply circuit 62. The constant current supply circuit 62, the electromotive force cell 24 and the resistor R are connected so as to constitute a current path for the small electric current (Icp).

The operational amplifier OP2 has an inverting input terminal connected to a Vcent point, an output terminal connected to the Ip+ terminal of the pump cell 14, and a non-inverting input terminal to which a reference voltage of +4V is applied. The PID control circuit 69 controls the pump current Ip in such manner that the potential developed across the Vs+ terminal of the electromotive force cell 24 connected through the operational amplifier OP1 and the Vcent point may be maintained at 450 mV. Specifically, the PID control circuit 69 performs a PID calculation of the deviation delta Vs between a target control value (450 mV) and a voltage (Vs) generated across the electromotive force cell 24, the deviation delta Vs is fed back to the operational amplifier OP2, and pump current Ip is passed through the pump cell 14.

Furthermore, the first-signal detection circuit 51 includes a detection resistance R1 which detects a pump current Ip and changes it into a voltage signal, and a differential amplification circuit 61 that performs differential amplification of voltage (difference of potential Vcent and potential $V_{PID}$) appearing across the detection resistance R1) and outputs it as a gas detection signal (VIp1).

In other words, the first-signal detection circuit 51 outputs a first gas detection signal (VIp1), which corresponds to a gas sensing signal (Ip+) of the first gas sensor 8, and the second-signal detection circuit 53 outputs a second gas detection signal (VIp2), which corresponds to the gas sensing signal (Ip) of the second gas sensor 9.

These gas detection signals (VIp1, VIp2) are outputted from the gas-detection signal terminal port 43 (referring to FIG. 1) to an external engine control unit, the terminal port 43 comprising a VIp1 terminal and a VIp2 terminal.

Then, the external engine control unit converts the gas detection signals to digital values by means of an A/D conversion circuit and then computes the oxygen concentration value from a predetermined map stored in the engine control unit. Based on the computed oxygen concentration value, the engine control unit detects the air-fuel ratio of the engine and controls it to a targeted optimum air-fuel ratio.

Next is a description of a resistance measurement of the electromotive force cell 24, as measured by the first-signal detection circuit 51. The subject resistance substantially represents the temperature of the gas sensor element 8.

In the first-signal detection circuit 51, the operational amplifier OP1 cooperates with a capacitor C1 and a switch SW1 to constitute a sample-and-hold circuit, turns the switch SW1 from ON to OFF when the resistance of the electromotive force cell 24 is measured, and retains the voltage Vs generated across the electromotive force cell 24 just before measurement, so as to enable the voltage Vs to be input to the PID control circuit 69.

An operational amplifier OP3 outputs the voltage value corresponding to a voltage difference between the value (voltage Vs of the electromotive force cell 24 just before applying a voltage for measuring its resistance) held by the operational amplifier OP1 and the electric potential Vsh when a constant current (Iconst) is passed through the electromotive force cell 24 for measuring its resistance. Since the voltage difference is proportional to the bulk resistance of the electromotive force cell 24 of the first gas sensor, it can be used as an internal resistance signal (Rpvs) of the gas sensor.

That is, the operational amplifier OP3 outputs the internal resistance signal Rpvs proportional to the bulk resistance of the electromotive force cell 24. In addition, the internal resistance signal Rpvs is proportional to the temperature of the electromotive force cell 24 as well as to the bulk resistance thereof.

A signal retention circuit 55 includes a known circuit comprising a capacitor and a switch, wherein a peak hold of the internal resistance signal Rpvs outputted from the operational amplifier OP3 starts when the switch provided in the signal retention circuit 55 is changed from OFF to ON. Then, when the switch is turned off after the predetermined period has lapsed just after the switch is turned on, the signal retention circuit 55 outputs the internal resistance signal Rpvs while holding its peak value.

In this way, the first-signal detection circuit 51 outputs the internal resistance signal Rpvs1 of the first gas sensor 8.

Notably, in the first-signal detection circuit 51, the switch SW1 controls the operational amplifier OP1, i.e., the sample and hold function. Further, the switch SW2 turns on and off an electric power source 63 to pass the constant current −Iconst for measuring the resistance of the electromotive force cell 24, and the switch SW3 turns on and off an electric power source 64 to pass a constant current +Iconst of polarity opposite that applied by the switch SW2.

Figure 4:
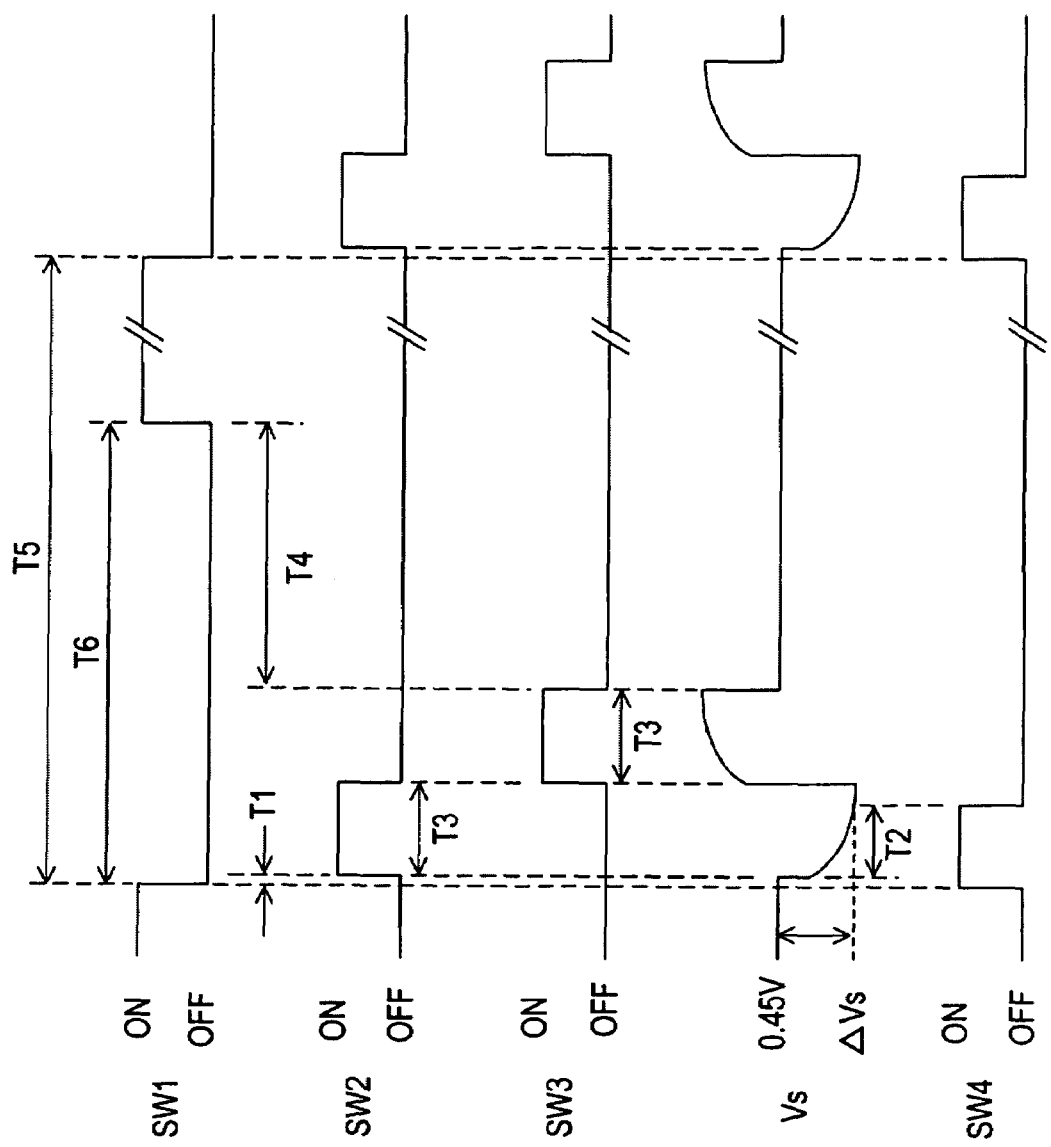
FIG. 4 is a timing chart of switches SW1, SW2, SW3, and SW4, and an explanatory view showing a waveform voltage Vs of an electromotive force cell.

The waveform of the voltage Vs generated at both ends of the electromotive force cell 24 are shown in FIG. 4 together with the timing chart of the switches SW1, SW2 and SW3. Further, a signal retention circuit 55 is illustrated with a block diagram in FIG. 3, and the timing chart of a switch SW4 (not shown) provided in the signal retention circuit 55 is also illustrated in FIG. 4.

The switch SW1 is turned off at predetermined intervals of T5 over a predetermined OFF time T6 (e.g., 500 μs), to enable measurement of the resistance of the electromotive force cell 24. In the meantime, during the OFF time T6, the input voltage to the PID control circuit 69 is maintained at 0.45V by the sample retention circuit composed of the operational amplifier OP1, etc.

Moreover, the timing when the switch SW1 is turned from ON to OFF is synchronized with turning the switch SW4 of the signal retention circuit 55 from OFF to ON. After the lapse of time T1 after the switch SW1 is turned off, the switch SW2 is turned on over a time T3 (about 100 μs), thus causing the constant current −Iconst for measuring the resistance to flow through the electromotive force cell 24 side. The polarity of the current −Iconst is opposite that of the internal electromotive force generated in the electromotive force cell 24, and by the effect of this current −Iconst, the voltage across both terminals of the electromotive force cell 24 is lowered by delta Vs as shown in the illustration.

In this connection, after the lapse of time T2 (about 60 μs) after application of the current −Iconst begins, the switch SW4 of the signal retention circuit 55 is turned from ON to an OFF state, and the peak value of the output (the internal resistance signal Rpvs) of the operational amplifier OP3 at that point of time (when 60 μs has lapsed after applying the current) is held in the signal retention circuit 55. Then, the signal retention circuit 55 holds the peak value of the internal resistance signal Rpvs until the time of subsequently energizing the current −Iconst together with outputting the internal resistance signal Rpvs held at that time.

Notably, the resistance value of the electromotive force 24 is measured when the time T2 of 60 μs has elapsed after the application of current −Iconst is started so that the resistance component at the interface between the porous electrode and the solid electrolyte is not included in the measured resistance. Namely, when the current or voltage for detection of such resistance is applied at a low frequency, the detected value includes a variation amount of the resistance component at the interface between the porous electrodes 22, 28 of the electromotive force cell 24 and the solid electrolyte. This variation amount is due to deterioration or the like of the interface, and if there is such variation it becomes impossible to carry out an accurate measurement. Conversely, measurement of resistance including a variation amount due to the interface deterioration can be detected by varying the measurement time and can be used to detect deterioration or malfunction of the gas sensor element per se.

After the lapse of time T3, the switch SW2 is turned off while at the same time the switch SW3 is turned on. The constant current +Iconst of polarity opposite the current −Iconst is applied to the electromotive force cell 24 side over the period T3 which is substantially the same as that during which the switch SW2 has been turned on. This is for decreasing the reset time for resetting or restoring a normal condition (from an abnormal condition in which the internal electromotive force is influenced by orientation of the oxygen ion conductive solid electrolyte constituting the electromotive force cell 24, and the electromotive force cell 24 is incapable of outputting an internal electromotive force representative of a correct oxygen content difference), and allowing the measurement of oxygen concentration to start again a short time after the resistance is measured.

When time T4 has lapsed after the lapse of time T3 for application of the constant current +Iconst, and after the switch SW3 is turned off, the switch SW1 is turned on to cause the electromotive force Vs of the electromotive force cell 24 to be applied again to the PID control circuit 69 by way of the operational amplifier OP1, whereby measurement of the oxygen content starts again by way of the PID controlling the pump current. After the lapse of the interval T5, the switch SW1 is turned off, whereby the resistance of the electromotive force cell 24 is measured again.

In addition, the internal resistance signal Rpvs is outputted outside the gas sensor control unit 1 by way of a signal-switching and outputting circuit 33. In this embodiment, the internal resistance signal Rpvs is output to the engine control unit, and the engine control unit controls energizing of the heater (not illustrated) for heating the gas sensor in such a manner that the value corresponding to the bulk resistance of the electromotive force cell 24 becomes equal to a target value based on the internal resistance signal Rpvs. This control substantially performs a function of maintaining the temperature of the gas sensor 8 accurately at a target temperature (800° C.) by making the voltage higher when the bulk resistance of the electromotive force cell 24 is higher than the target value and making it lower when lower than the target value.

Returning to FIG. 1, plural signals are inputted to the switch output portion 33, and the switch output portion 33 outputs a single signal at a time by switching these incoming signals as a switched output signal. Notably, the signal-switching and outputting circuit 33 can constitute a multiplexer.

In the input side of the signal-switching and outputting circuit 33, a first internal resistance signal Rpvs1, a second internal resistance signal Rpvs2 and a voltage value signal of each terminal (Vs+1 terminal, COM1 terminal, Ip+1 terminal, Vs+2 terminal, COM2 terminal and Ip+2 terminal) of a sensor connection terminal portion 39 are inputted, respectively.

An anomaly-detection circuit 37 detects a voltage anomaly at the connecting point between a signal detection portion 31 and the gas sensors 8, 9 by judging whether or not the voltage value of each terminal (Vs+1 terminal, COM1 terminal, Ip+1 terminal, Vs+2 Ip+2 terminal) of the sensor connection terminal portion 39 is within normal limits.

The anomaly-detection circuit 37, in advance, stores the normal range of each terminal in the sensor connection terminal portion 39 as a reference value range and compares the reference value range with the voltage value of each terminal. When the voltage value of a terminal is within the reference value range, the subject terminal is deemed to be normal. The subject terminal is deemed to exhibit an anomaly when it deviates from the reference value range. Then, the anomaly-detection circuit 37 outputs a voltage anomaly notification signal, which denotes the voltage anomaly, to the engine control unit by way of a serial communication terminal 45, when a voltage anomaly is detected.

A switched-signal controlling circuit 35 outputs a switch control signal to the signal-switching and outputting circuit 33, and controls the signal-switching and outputting circuit 33 so as to determine a switched output signal to be outputted from the signal-switching and outputting circuit 33. Here, the flow chart showing the contents of the signal control processing at the switched-signal controlling circuit 35 is shown in FIG. 5.

Figure 5:
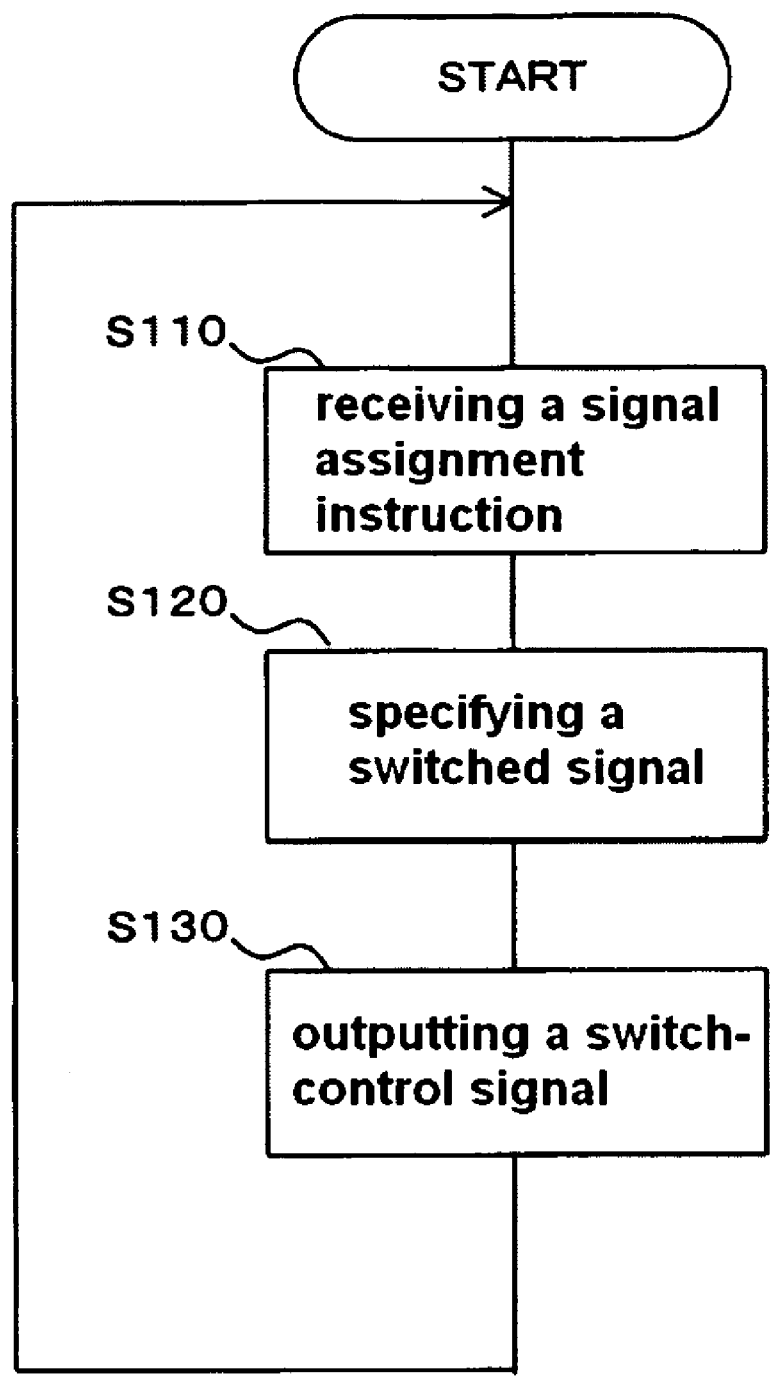
FIG. 5 is a flow chart showing the contents of a signal control processing in a switched-signal controlling circuit.

As shown in FIG. 5, in step S110, a signal assignment instruction from the engine control unit is received.

In addition, the switched-signal controlling circuit 35 transmits and receives various signals with an external apparatus connected by way of the serial communication terminal 45, and receives various signals, such as a signal assignment instruction, from the engine control unit through serial communication.

Next, in S120, the process specifying the signal that is to be outputted as the switched output signal is performed based on the signal assignment instruction, which has been received.

Notably, since the signal assignment instruction transmitted from the engine control unit is set, in advance, in the engine control unit so as to correspond to the various types of signals output from the signal-switching and outputting circuit 33, the switched-signal controlling circuit 35 can specify the switched output signal in each case based on the signal assignment instruction.

In S130, a switch control signal is determined so that the signal which the engine control unit requires may be output as the switched output signal based on a result of S120, and the switching control signal, which has been determined, is output to the signal-switching and outputting circuit 33.

In addition, the signal-switching and outputting circuit 33 determines a signal that is to be outputted as the switched output signal among plural incoming signals based on the switch control signal from the switched-signal controlling circuit 35, to thereby output a single signal as the switched output signal by switching plural incoming signals.

After the process of S130 is completed, the signal process returns to S110.

Thus, by repeating the process from S110 to S130, the switched-signal controlling circuit 35 controls the signal-switching and outputting circuit 33 based on the signal assignment instruction from the external engine control unit. The switched-signal controlling circuit 35 determines the switched output signal, to thereby output the switched output signal according to a demand from the engine control unit.

In the meantime, the engine control unit performs a signal assignment instruction, which differentiates a signal outputted as a switched output signal when the anomaly-detection circuit 37 indicates a voltage anomaly at the connecting point from the other signal when no anomaly at the connecting point is indicated by the anomaly-detection circuit 37.

Specifically, when no voltage anomaly at the connecting point is indicated by the anomaly-detection circuit 37, the engine control unit (ECU) transmits the signal assignment instruction to the switched-signal controlling circuit 35. The ECU instructs that the first internal resistance signal Rpvs1 and the second internal resistance signal Rpvs2 are to be alternatively output as the switched output signal from the signal-switching and outputting circuit 33 at predetermined intervals by way of the serial communication terminal 45. Further, when a voltage anomaly at the connecting point is indicated by the anomaly-detection circuit 37, the engine control unit sequentially transmits a signal assignment instruction to the switched-signal controlling circuit 35, instructing that the voltage value signal of each terminal in the sensor connection terminal portion 39 (Vs+1 terminal, COM1 terminal, Ip+1 terminal, Vs+2 terminal, COM2 terminal and Ip+2 terminal) is to be alternatively transmitted as the switched-signal output.

That is, the gas sensor control unit 1 informs the engine control unit of the occurrence of an anomaly by way of the serial communication terminal 45 when any voltage anomaly of any of the terminals in the sensor connection terminal portion 39 is detected by the anomaly-detection circuit 37. Then, the gas sensor control unit 1 sequentially switches and outputs the voltage value signal of each terminal in the sensor connection terminal portion 39 as the switched output signal based on the signal assignment instruction sequentially transmitted from the engine control unit to the switched-signal controlling circuit 35 by way of the serial communication terminals 45.

In the gas sensor control unit 1 according to the invention, the first-signal detection circuit 51 and the second-signal detection circuit 53 are within the scope of the plural signal detection means, the signal-switching and outputting circuit 33 is within the scope of the signal-switching and outputting means, the switched-signal controlling circuit 35 is within the scope of the switched output signal control means, and the gas detection signal terminal port 43 is within the scope of the gas detection signal output means. Moreover, the signal retention circuit 55 is within the scope of the resistance signal retention means, and the anomaly-detection circuit 37 is within the scope of the anomaly detection means and the voltage anomaly notification means. S110 and the serial communication terminal 45 in the signal control process of the switched-signal controlling circuit 35 are within the scope of the signal assignment instruction receiving means, and the pump cell 14 and the electromotive force cell 24 of the gas sensors 8, 9 are included in the meaning of the gas-sensing solid electrolyte element of the gas sensor.

As explained above, the gas sensor control unit 1 switches and outputs any one of the signals among the first internal resistance signal Rpvs1, the second internal resistance signal Rpvs2 and the voltage value signal of each terminal (Vs+1 terminal, COM1 terminal, Ip+1 terminal, Vs+2 terminal, COM2 terminal and Ip+2 terminal) in the sensor connection terminal portion 39 from the switched-signal output terminal 41. This is realized by the signal-switching and outputting circuit 33 which is capable of switching two or more inputted signals and outputting any one of them alternatively in sequential order.

That is, when the gas sensor control unit 1 outputs plural signals (the first internal resistance signal Rpvs1, the second internal resistance signal Rpvs2 and the voltage value signal of each terminal in the sensor connection terminal portion 39) relating to plural gas sensors, the gas sensor control unit can output each signal via the single signal-switching and outputting circuit 33 rather than an individual signal output means for each signal as in the case of a conventional control unit. Accordingly, the number of signal output portions and signal paths which output signals to the engine control unit can be reduced by having the single signal-switching and outputting circuit 33 instead of having plural signal output means, thereby facilitating a simple configuration and reasonable cost of the gas sensor control unit 1.

Especially, since the gas sensor control unit 1 switches and outputs at least two internal resistance signals Rpvs 1, Rpvs 2 by using the single signal-switching and outputting circuit 33, the number of output means for outputting these internal resistance signals Rpvs1, Rpvs2 to the engine control unit can assuredly be reduced.

Further, the first-signal detection circuit 51 and the second-signal detection circuit 53 in the signal detection portion 31 comprise the signal retention circuit 55 respectively, which holds (performs a peak hold) the internal resistance signals Rpvs.

In addition, during operation of the gas sensor control unit 1, the internal resistance signal Rpvs representing the bulk resistance of the electromotive force cell 24 is not necessarily detected regularly as is the case for the gas detection signals VIp1 and VIp2. Rather, Rpvs is detected so as to enable the gas sensor control unit to output the gas sensor element resistance at a specific time, which varies in connection with the time lapse, to the external apparatus (the engine control unit). Therefore, since the signal retention circuit 55 can hold the internal resistance signal Rpvs at a specific time, the output timing of Rpvs to the engine control unit can be determined at any specific time during a retention period thereof.

Thus, when switching and outputting plural internal resistance signals Rpvs in the signal-switching and outputting circuit 33, the output timing of each internal resistance signal Rpvs can be freely determined, whereby each internal resistance signal Rpvs from the gas sensors 8, 9 can more flexibly be outputted to the engine control unit.

Further, the gas sensor control unit 1 may not switch the gas detection signals (VIp1 and VIp2) detected in the signal detection portion 31 and may not output them alternatively by way of the signal-switching and outputting circuit 33, but can independently output plural gas detection signals (VIp1 and VIp2) from the gas detection signal terminal 43, whereby these important gas detection signals are outputted to the engine control unit on a regular frequent basis.

According to the gas sensor control unit 1 constituted as described above, the up-dated gas detection signals (VIp1 and VIp2 signals) of plural gas sensors can be outputted to the external apparatus at any time, and the gas detection signals (VIp1 and VIp2 signals) can be adequately outputted to the engine control unit which requires plural gas detection signals on a regular frequent basis. Thereby, the engine control unit is capable of performing more accurate air-fuel ratio control.

Furthermore, since the gas sensor control unit 1 receives the signal assignment instruction from the engine control unit by way of serial communication and can share the serial communication terminal 45 with signals other than the assignment instruction signal, any exclusive terminal space used for providing the signal assignment instruction is not required, thereby reducing the cost of the gas sensor control unit 1.

Although a preferred embodiment of the present invention has been described above, the present invention is not limited thereto. Various modifications and variations can be made thereto within the spirit and scope of the invention.

For example, the gas detection signals (VIp1 and VIp2 signals) are normally outputted from the gas detection signal terminal 43 in the configuration of the above-mentioned embodiment, however, a configuration where the gas detection signals are switched and outputted by way of the signal-switching and outputting circuit 33 may also be employed.

Further, the invention is not limited to a configuration where the switched output signal is determined based on the signal assignment instruction from the engine control unit, which is the external apparatus, in order to synchronize with the contents of the switched output signal. Rather, the invention may be configured such that the gas sensor control unit determines the contents of the switched output signal, and outputs an output content identification signal for identifying the content of the signal to the external apparatus in order to synchronize with the contents of the switched output signal.

Thus, the invention is not limited to a configuration where the external apparatus (engine control unit) determines the switched output signal, however, the invention may be configured such that the gas sensor control unit determines the switched output signal.

In addition, the output content identification signal may be outputted from the exclusive output terminal to the external apparatus, or may be outputted to the external apparatus by way of serial communication.

Then, when determining the switched output signal in the gas sensor control unit, for example, signals may be sequentially switched in a regular cycle, or may be sequentially switched and outputted in a different output cycle determined for each signal.

Moreover, the gas sensor control unit may have plural signal-switching and outputting circuits in order to output plural switched output signals. For example, the gas sensor control unit may be configured such that it may have a resistance signal-switching and outputting circuit which switches and outputs plural internal resistance signals (Rpvs1 and Rpvs2) and a gas detection signal-switching and outputting circuit which switches and outputs plural gas detection signals (VIp1 and VIp2).

Then, when a voltage anomaly occurs at any one of the sensor connection terminals, the gas sensor control unit does not necessarily have a configuration where all the voltage value signals including a signal indicating normal state terminal are outputted. Instead, a voltage value signal relating to a terminal which tends to generate an anomaly may be switched and outputted. In the case where there is no anomaly at the terminal, the external apparatus may be arranged such that the voltage value signals of other terminals are switched and outputted.

Further, the number of gas sensors being controlled is not necessarily limited to two sensors, but can comprise three or more sensors.

Notably, when controlling three or more gas sensors, the configuration of each portion (the number of signal detection circuits in the signal detection portion, the number of input terminals in the signal-switching and outputting circuit, the contents of the control processing in the switched-signal controlling circuit, the number of input terminals in the anomaly-detection circuit, etc.) should correspond to the number of gas sensors in order to control each gas sensor.

This application is based on Japanese Patent application JP 2005-104519, filed Mar. 31, 2005, the entire content of which is hereby incorporated by reference, the same as if set forth at length.

What is claimed is:

1. A gas sensor control unit adapted for connection to plural gas sensors including at least first and second gas sensors, comprising:

first and second signal-detection circuits for detecting first and second gas-detection signals and first and second internal resistance signals of the first and second gas sensors, respectively;

a signal-switching and outputting circuit for receiving signals including said first and second internal resistance signals, said signal-switching and outputting circuit switching the signals including at least said first and second internal resistance signals, and outputting at least one of the switched signals from the signal-switching and outputting circuit to an external apparatus;

a switched-signal controlling circuit for controlling said signal-switching and outputting circuit and specifying the signals to be switched and outputted from the switched-signal controlling circuit to the external apparatus; and a gas detection signal output means for independently outputting plural gas detection signals detected by the first and second signal detection circuits to the external apparatus without passing through the signal-switching and outputting circuit.

2. The gas sensor control unit as claimed in claim 1, wherein each of plural signal detection circuits includes a resistance signal retention circuit for holding a detected internal resistance signal of an associated gas sensor, and outputting the internal resistance signals held by the resistance signal retention circuit to the signal-switching and outputting circuit.

3. The gas sensor control unit as claimed in claim 1, wherein the switched-signal controlling circuit for controlling the signal-switching and outputting circuit receives a signal assignment instruction from the external apparatus by way of serial communication, the signal assignment specifying which of the switched signals are to be outputted from the signal-switching and outputting circuit.

4. The gas sensor control unit as claimed in claim 1, further comprising an anomaly detection circuit for detecting a voltage anomaly appearing at any of plural connecting points connecting the signal detection circuits with the plural gas sensor elements and for notifying the external apparatus of the voltage anomaly.

5. The gas sensor control unit as claimed in claim 1, further comprising:

an anomaly detection circuit for detecting a voltage anomaly appearing at any of plural connecting points connecting said first and second detection circuits with said gas sensors and for outputting a voltage anomaly notification signal notifying the external apparatus of the occurrence of the voltage anomaly.

6. The gas sensor control unit as claimed in claim 1, wherein the signals received by the signal-switching and outputting circuit includes signals detected at a sensor connection terminal portion connecting the sensors with the gas sensor control unit.

* * * * *